(12) United States Patent
Cosolito

(10) Patent No.: US 10,918,201 B2
(45) Date of Patent: Feb. 16, 2021

(54) BRUSH CLEANING DEVICE USING UV LIGHT TO DRY, SANITIZE, AND DISINFECT COSMETIC BRUSHES

(71) Applicant: Lisa Cosolito, Glen Cove, NY (US)

(72) Inventor: Lisa Cosolito, Glen Cove, NY (US)

(\*) Notice: Subject to any disclaimer, the term of this patent is extended or adjusted under 35 U.S.C. 154(b) by 50 days.

(21) Appl. No.: 16/295,113

(22) Filed: Mar. 7, 2019

(65) Prior Publication Data

US 2019/0274421 A1  Sep. 12, 2019

Related U.S. Application Data

(60) Provisional application No. 62/640,212, filed on Mar. 8, 2018.

(51) Int. Cl.
| | | |
|---|---|---|
| *A46B 17/06* | (2006.01) | |
| *B08B 11/02* | (2006.01) | |
| *B08B 7/00* | (2006.01) | |
| *A61L 2/10* | (2006.01) | |
| *F26B 3/00* | (2006.01) | |

(52) U.S. Cl.
CPC ........... *A46B 17/065* (2013.01); *A46B 17/06* (2013.01); *A61L 2/10* (2013.01); *B08B 7/0057* (2013.01); *B08B 11/02* (2013.01); *F26B 3/00* (2013.01); *A46B 2200/1046* (2013.01)

(58) Field of Classification Search
CPC .............. A46B 17/065; A46B 17/06; A46B 2200/1046; A61L 2/10; B08B 7/0057; B08B 11/02; F26B 3/00
See application file for complete search history.

(56) References Cited

U.S. PATENT DOCUMENTS

2003/0034459 A1\* 2/2003 Bonin ...................... A61L 2/06
 250/491.1
2006/0175554 A1\* 8/2006 Riddell ..................... A61L 2/10
 250/455.11

\* cited by examiner

*Primary Examiner* — Nicole M Ippolito
*Assistant Examiner* — Hanway Chang
(74) *Attorney, Agent, or Firm* — Carter, DeLuca & Farrell LLP; Francesco Sardone, Esq.

(57) ABSTRACT

A dryer, sanitizer, and disinfecting device for make-up brushes includes an outer housing having an upper surface defining a plurality of openings therein with the plurality of openings arranged in a linear array; an inner housing including a retainer having a plurality of recesses corresponding to the plurality of openings defined in the outer housing; and a sterilizing component supported within at least one of the outer housing or the inner housing, wherein the sterilizing component effects the cleaning chamber, and wherein the sterilizing component includes a UV light bulb.

15 Claims, 7 Drawing Sheets

BRUSH CLEANING DEVICE USING UV LIGHT TO DRY, SANITIZE, AND DISINFECT COSMETIC BRUSHES

CROSS-REFERENCE TO RELATED APPLICATION

The present application claims the benefit of and priority to U.S. Provisional Patent Application Ser. No. 62/640,212, filed on Mar. 8, 2018, the entire content of which is incorporated herein by reference.

BACKGROUND

Technical Field

The present disclosure relates to devices for cleaning and killing bacteria on personal care instruments, more particular to a dryer, sanitizer, and disinfecting device for brushes, applicators or the like (e.g., make-up or cosmetic).

Background of Related Art

Brushes are instruments or tools used for application and/or smoothing of cosmetics, styling/cleaning/detangling of hair, and/or for grooming animal fur and the like. Most brushes consist of a flexible brush side or head including tightly clustered bristles mounted on a handle.

Today, much is being said and written about the dangers of contaminated make up brushes. One recommendation is that make-up brushes be replaced every two or three weeks. Another suggestion is that make-up brushes be sterilized after each use so that a high quality brush with superior make-up application properties can be affordable and still not become a breeding ground for bacteria.

SUMMARY

Accordingly, an object of this disclosure is to provide a new and novel device for and methods of sterilizing and cleaning make-up or cosmetic brushes, for example, hair brushes, eyelash brushes, facial brushes, and the like. Here an ultra-violet (UV) light make-up brush dryer, sanitizer, and disinfecting device is presented.

According to an aspect of the present disclosure, a dryer, sanitizer, and disinfecting device for make-up brushes is provided. The device includes an outer housing having an upper surface defining a plurality of openings therein, the plurality of openings being arranged in a linear array.

The device further includes an inner housing disposed within the outer housing. The inner housing includes a retainer projecting from an inner surface thereof, wherein the retainer includes a plurality of recesses corresponding to the plurality of openings defined in the upper surface of the outer housing. The plurality of recesses and the plurality of openings are in registration with one another.

The device also includes a door secured to at least one of the outer housing or the inner housing, wherein the door is configured to selectively open the device to provide access to a cleaning chamber defined by at least one of the outer housing or the inner housing.

The device includes a sterilizing component supported within at least one of the outer housing or the inner housing. The sterilizing component effects the cleaning chamber. The sterilizing component includes a UV light bulb.

The device further includes an electronic circuit connected to the sterilizing component for selective activation of the sterilizing component.

The UV light bulb may extend across substantially an entire length of the cleaning chamber.

The UV light bulb may extend along a bottom of the cleaning chamber.

The UV light bulb may define a longitudinal axis that extends along a plane defined by the openings of the outer housing and by the recesses of the retainer.

At least a portion of the UV light bulb may be in registration with each opening of the outer housing and each recess of the retainer.

The sterilizing component may include a heating element.

The sterilizing component may include at least one of a heating element or a fan.

The device may further include control components connected to the electronic circuit and each of the UV light bulb, the heating element and the fan, wherein the control components control activation of each of the UV light bulb, the heating element and the fan.

The control component may include a timer.

Each opening of the outer housing may include a rubber-like retainer extending into the opening and extending substantially orthogonally from the opening, for increasing friction with a make-up brush loaded into the device.

The rubber-like retainer may include a drape extending from opposite sides of the opening of the outer housing and spanning the opening to define a slit therebetween.

The rubber-like retainer may include a stem projecting orthogonally from the opening of the outer housing, wherein the stem has a c-shaped transverse, cross-sectional profile that defines a slit that is in registration with the slit defined by the rubber drape of the opening of the outer housing.

Each recess of the inner housing may include a rubber-like retainer extending into the opening and extending substantially orthogonally from the opening, for increasing friction with a make-up brush loaded into the device.

The rubber-like retainer may include a drape extending from opposite sides of the recess of the inner housing and spanning the recess to define a slit therebetween.

The rubber-like retainer may include a stem projecting orthogonally from the recess of the inner housing, wherein the stem has a c-shaped transverse, cross-sectional profile that defines a slit that is in registration with the slit defined by the rubber drape of the recess of the inner housing.

The door may be at least partially transparent.

BRIEF DESCRIPTION OF THE DRAWINGS

In the following, the embodiments of disclosure will be described in detail with reference to the following attached figures.

DETAILED DESCRIPTION

Figure 1:
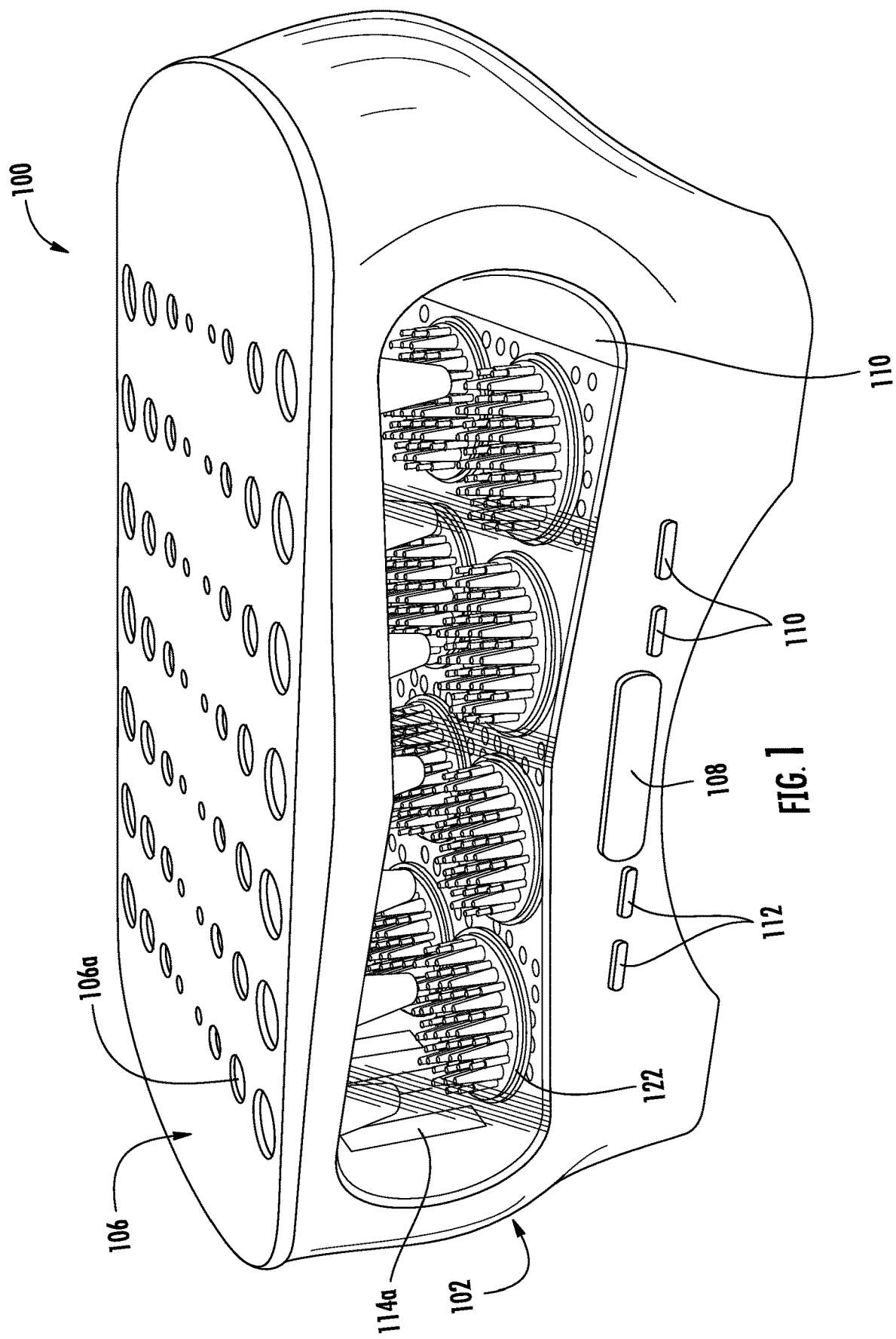
FIG. 1 is a perspective view of an ultra-violet (UV) light make-up brush dryer, sanitizer, and disinfecting device according to an embodiment of the present disclosure.
Figure 2:
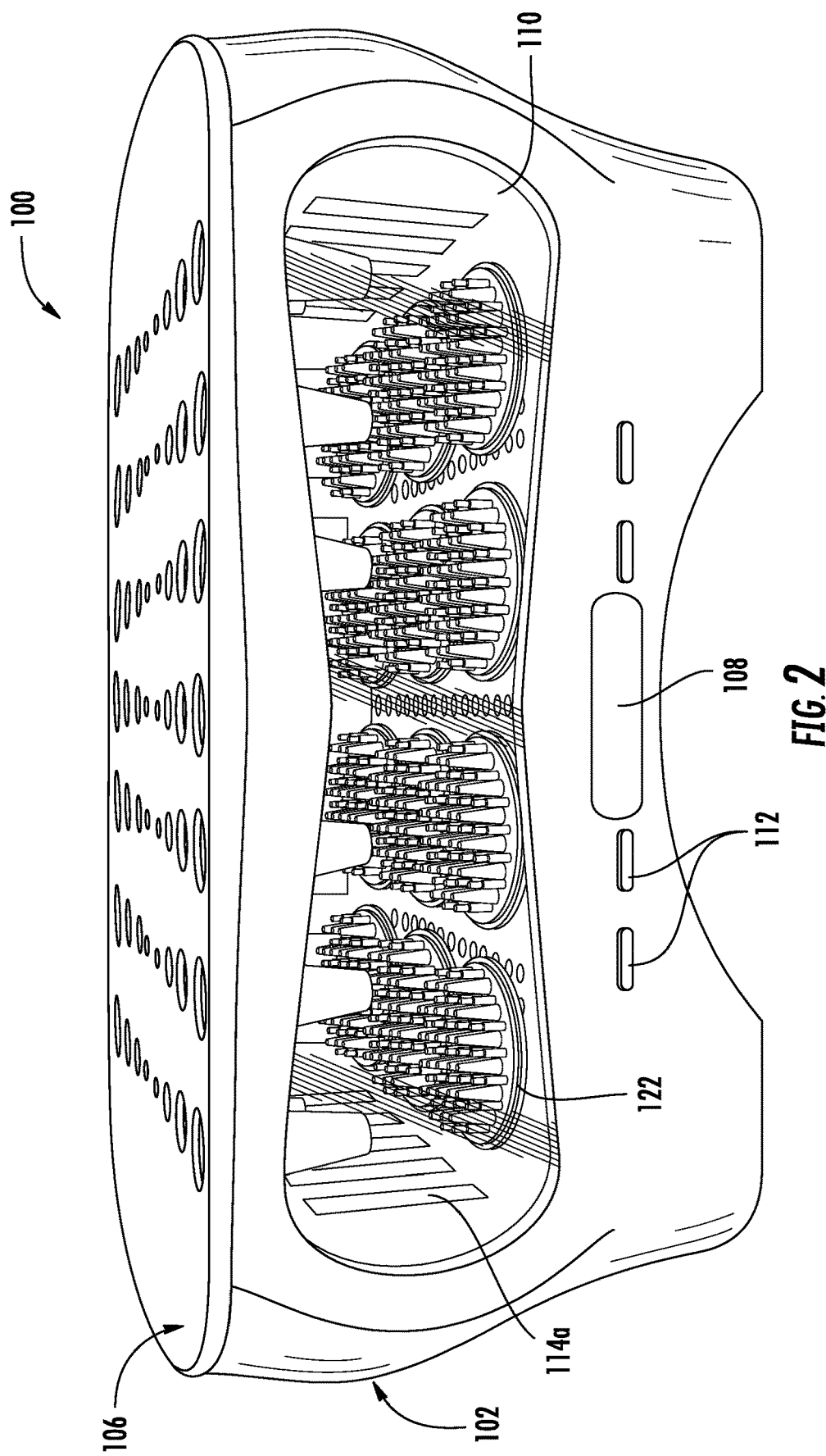
FIG. 2 is front, elevational view of the device of FIG. 1.
Figure 3:
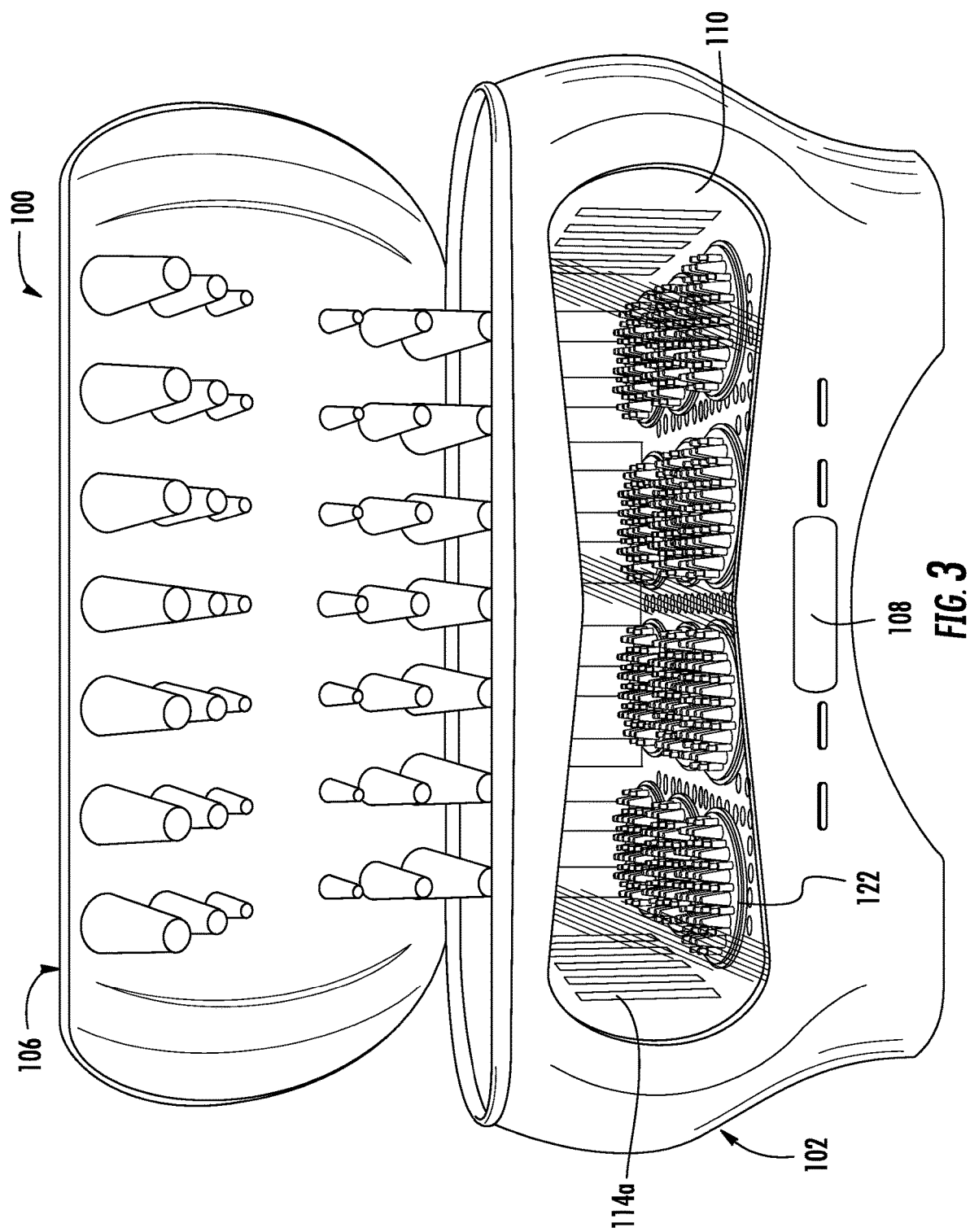
FIG. 3 is front, elevational view of the device of FIG. 1, with a lid thereof open.
Figure 4:
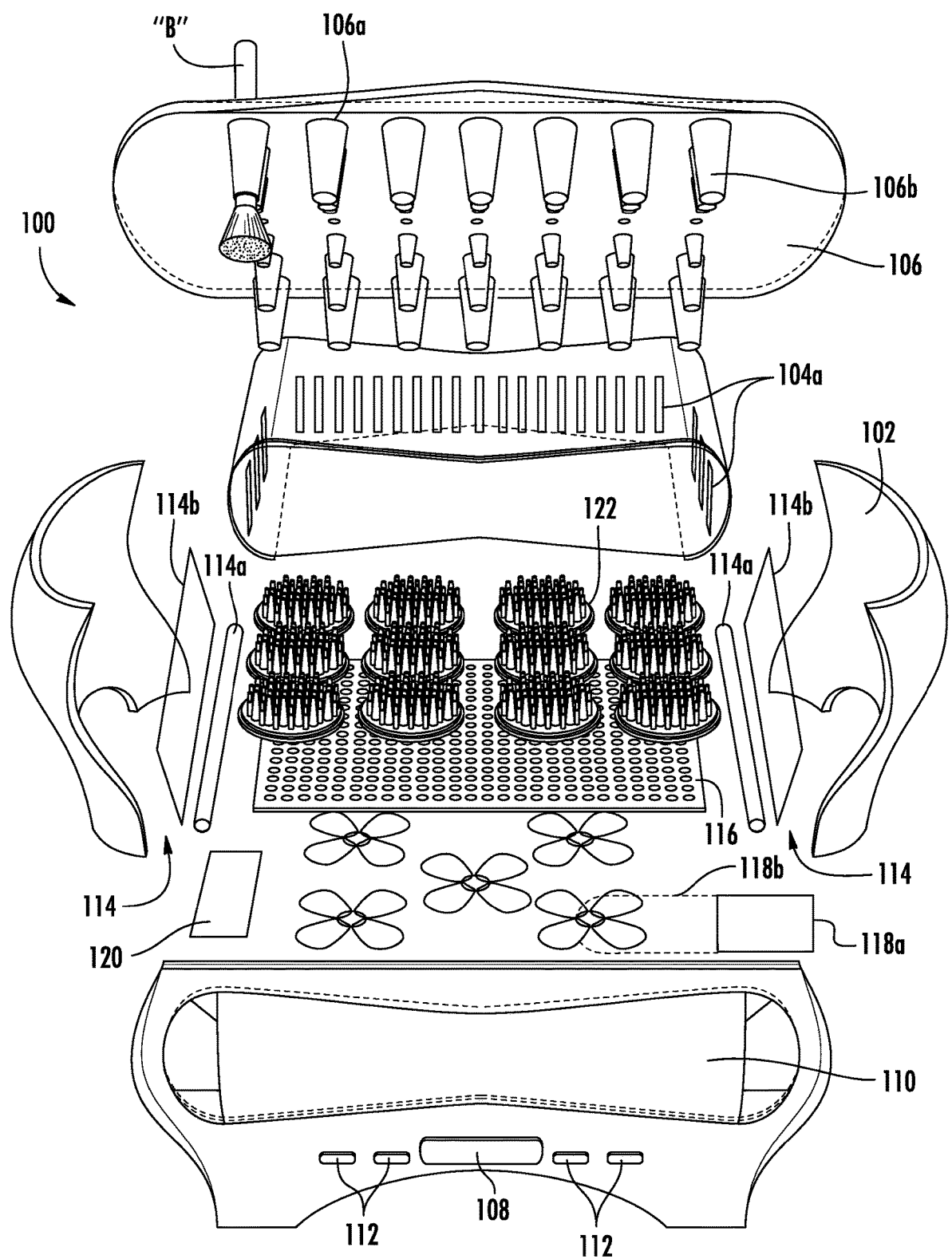
FIG. 4 is a perspective view, with parts separate, of the device of FIGS. 1-3.

Presently, embodiments of the current disclosure relate to a UV light make-up brush dryer, sanitizer, and disinfecting device, and configurations thereof, that is designed to receive, hold, and process one or multiple cosmetic or make-up applying brushes "B". In embodiments, with reference to FIGS. 1-4, the UV light make-up brush cleaner, dryer, sanitizer, and disinfecting device or brush cleaning device 100 (hereinafter, "the brush cleaning device") may include an outer shell or housing 102, an inner shell or housing 104, a lid 106, a display 108, a window 110, control components 112, a sterilizing component 114, a support grill 116, at least one fan 118, an electronic circuit 120, and at least one bristled brush 122.

The shape of the outer shell 102 may be generally oval, rectangular or cylindrical. The outer shell 102 of the brush cleaning device 100 may be manufactured of a plastic or other suitable material, it may be of a one-piece construction or it may include several pieces. Further, the material used to make the outer shell 102 can be a highly reflective material or it may include a highly reflective surface or coating. In other embodiments, an interior surface of the outer shell 102 may be an arcuate surface or may have any suitable shape; however, in embodiments, it may be of a shape that can enable focusing of light and/or heat into the interior of the brush cleaning device 100 and it may additionally be configured to enclose most of the light inside of the brush cleaning device 100. For example, the interior surface of outer shell 102 may form a generally parabolic shape for focusing the energy from the sterilizing component (e.g., UV light or heat source) 114.

The inner shell 104 may be constructed of similar materials and shape as the outer shell. In embodiments, the inner shell 104 may include a UV light reflecting material or coating on its interior surface. It is understood that a number of additional safety features may be included to prevent the UV light from escaping from the housing. Further, the inner shell 104 may include multiple openings 104a to enable air circulation and drainage. The shape of the inner shell 104 may be a substantially elongated rectangle with an opening configured to receive the supporting grill 116. The supporting grill 116 may be configured to collect make-up brush drippings and debris; and further configured to connect to the at least one bristled brush 122.

In embodiments, the supporting grill 116 may be constructed of a UV light reflecting material and it may include a plurality of openings or perforations 116a which may serve as air circulation, cooling or drainage holes.

Below the supporting grill 116, at least one fan 118 may be connected to a first motor 118a, via gears, belts or the like 118b, and it may be configured to circular air along the interior of the brush cleaning device 100. Further, the first motor 118a, or a second motor (not shown), may be configured to drive rotation of the at least one bristle brush 122, via gears, belts or the like (not shown). Each bristle brush 122 may be configured to rotate and to assist with cleaning of a make-up brush "B" which may be received by the brush cleaning device 100 via the lid 106. Each bristle brush 122 may be fabricated from or include rubber or nylon bristles extending upwardly toward the lid 106 of the brush cleaning device 100. The motor(s) 118a may be connected to electronic circuit 120 for receiving control signals therefrom.

In embodiments, the lid 106 may include at least one opening 106a formed therein and configure to receive a make-up brush "B". The lid 106 may support a brush stabilizer 106b which is in registration with the at least one opening 106a formed therein, and it may be further configured to support a make-up brush "B" in a brush or bristle down orientation, and such that the bristles of the make-up brush "B" are engagable by the bristled brushes 122. The lid 106 may be hinged or releasably attached to the outer shell 102 or other components of the brush cleaning device 100, and provide the user with selective access to a cleaning chamber defined within the outer shell 102 and/or the inner shell 104.

The sterilizing component 114 may include at least one UV light bulb, or the like, 114a, and, optionally, at least one heating element 114b. The sterilizing component 114 may be connected to electronic circuit 120 for receiving control signals therefrom. The sterilizing component 114 may be interposed between the outer shell 102 and the inner shell 104.

While in use, brush cleaning device 100 may be connected to a power source (A/C, D/C, battery, etc.), next, a make-up brush "B" may be inserted via an opening 106a of the lid 106 passing thought the bush stabilizer 106a and lastly close lid 106 in order to engage the bristles of the make-up brush "B" with the at least one bristled brush 122. The user then may turn on the cleaning device using an on/off switch of control component 112 connected to the electronic circuit 120, select powering of the at least one bristled brush 122, the sterilizing component 120 (e.g., the UV light bulb 114a, the heating element 114b, or both), and/or the fan 118 via their respective control components or buttons 112.

Figure 5:
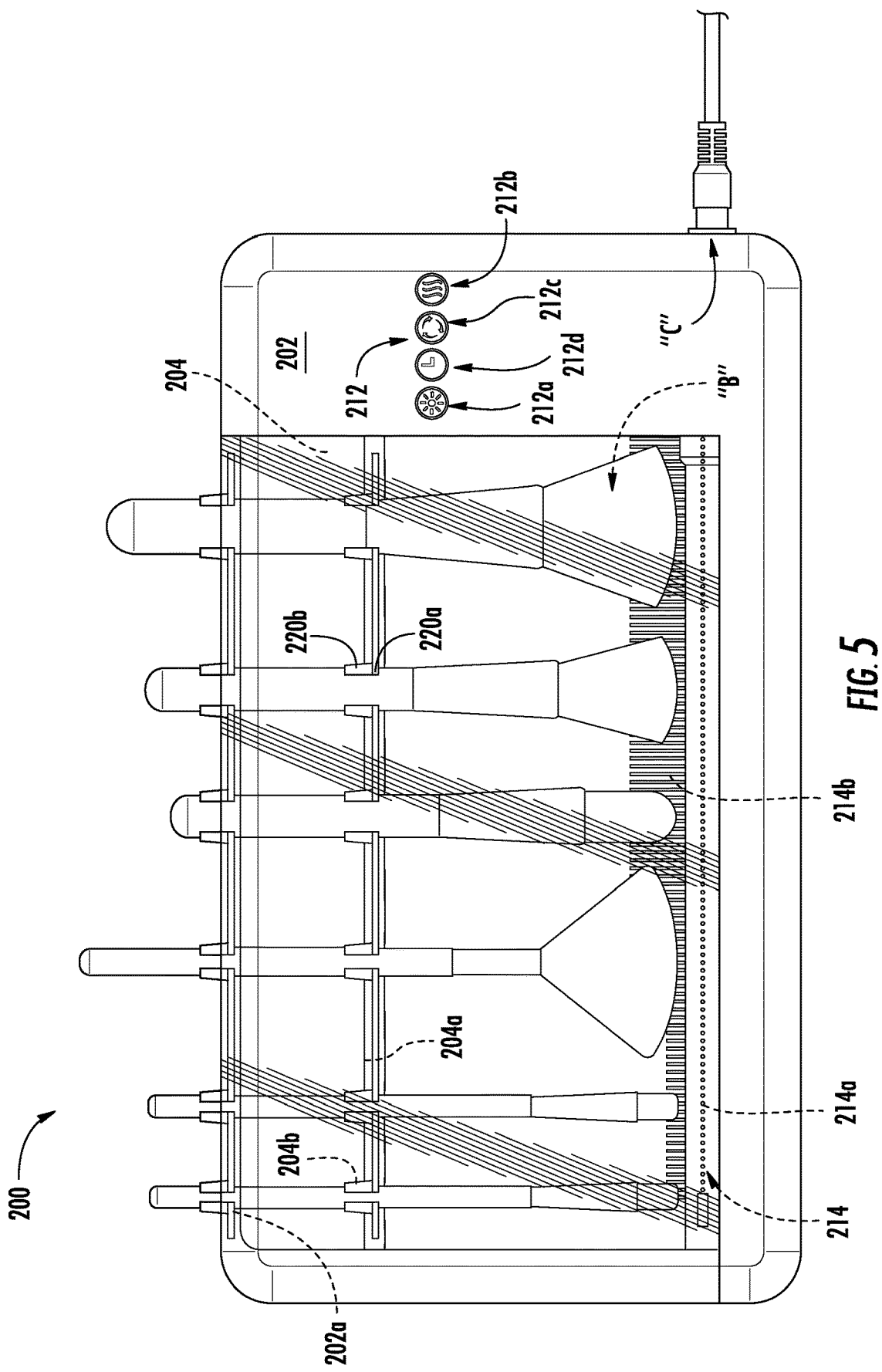
FIG. 5 is a front, elevational view of an ultra-violet (UV) light make-up brush dryer, sanitizer, and disinfecting device according to another embodiment of the present disclosure.
Figure 6:
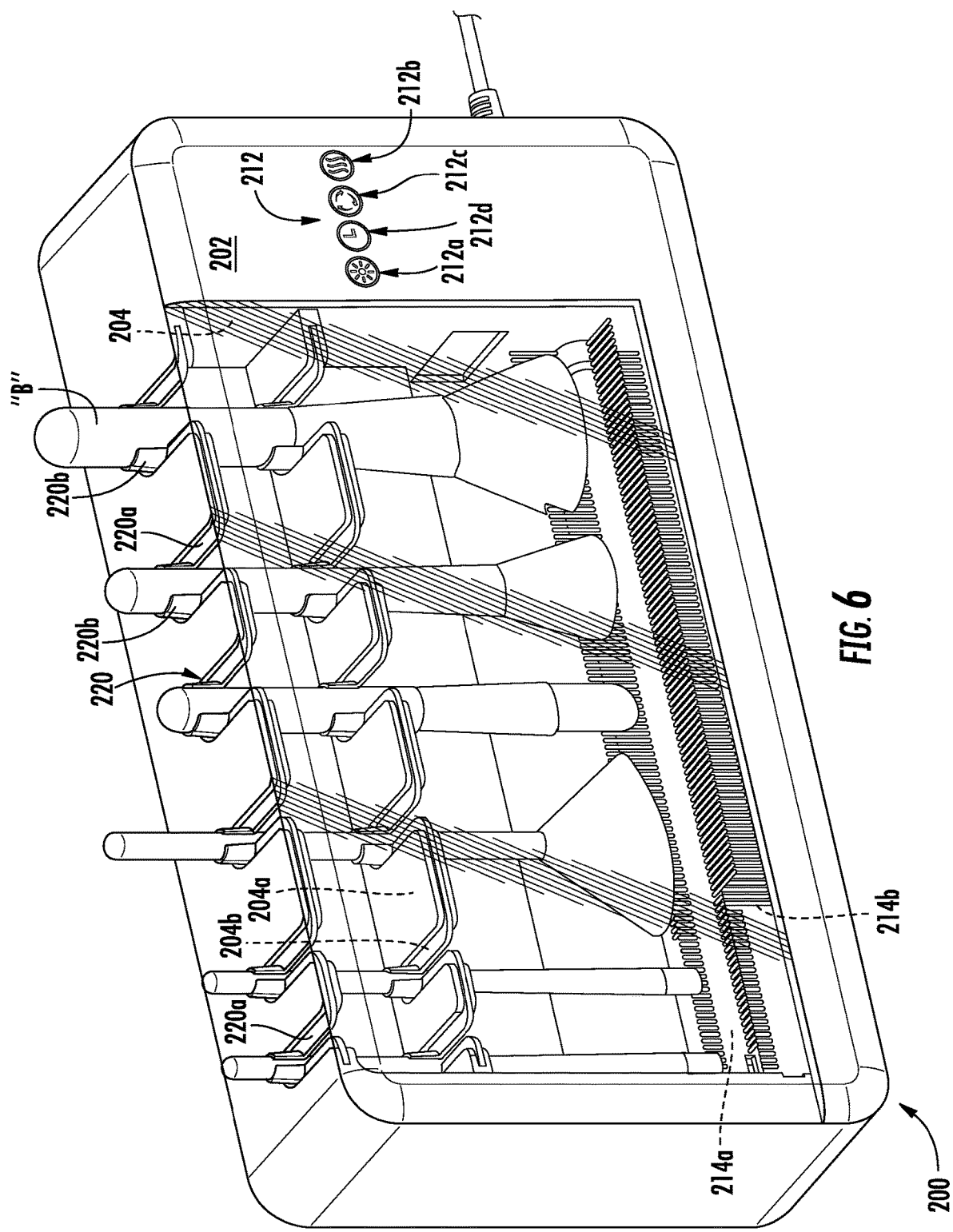
FIG. 6 is a front, perspective view of the device of FIG. 5.
Figure 7:
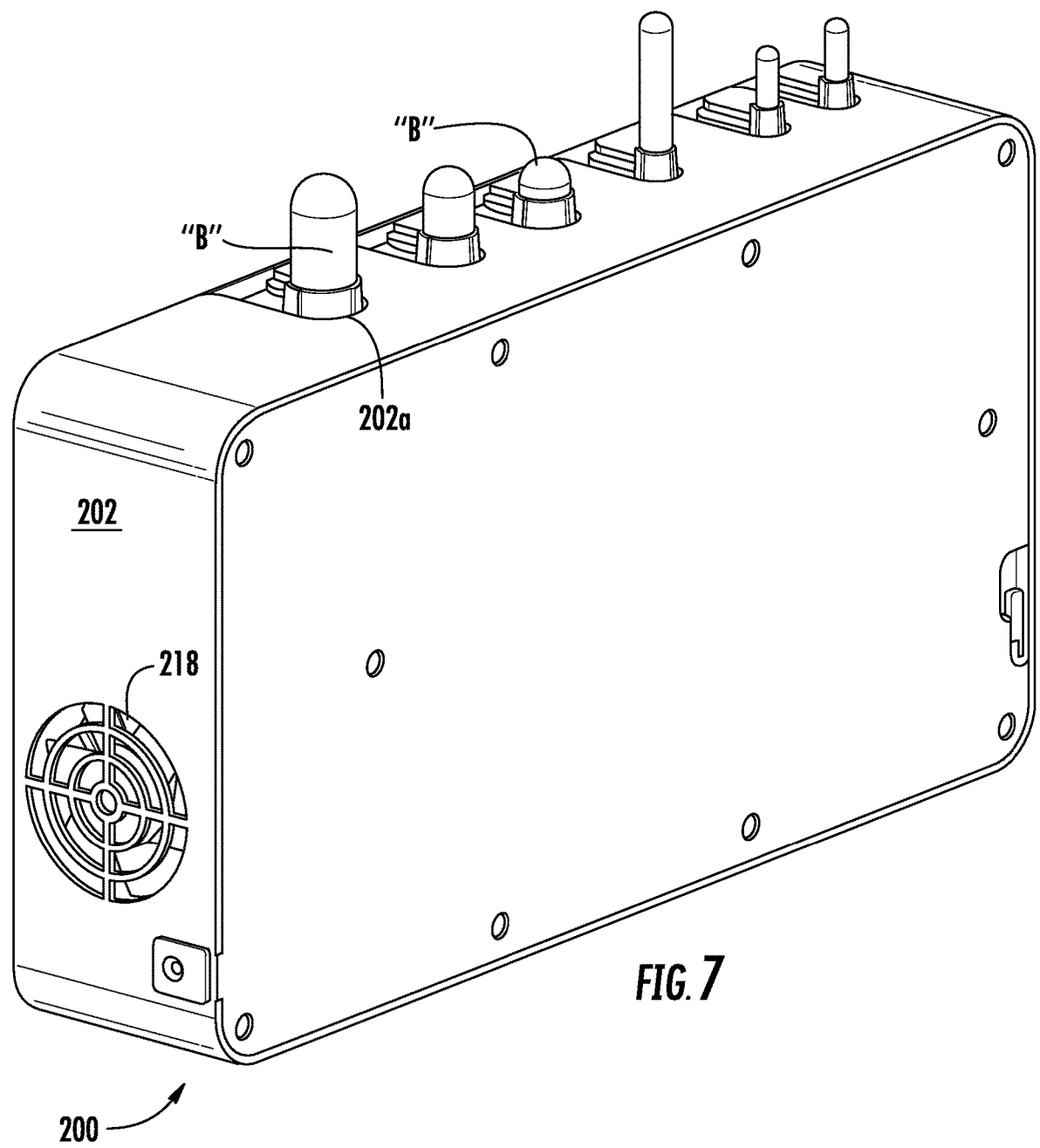
FIG. 7 is a rear, perspective view of the device of FIGS. 5 and 6.

Turning now to FIGS. 5-7, a brush cleaning device, according to another embodiment of the present disclosure is shown, and is generally designated as brush cleaning device 200. Brush cleaning device 200 includes substantially similar components as brush cleaning device 100, and functions in a manner substantially similar to brush cleaning device 100. Accordingly, in the interest of brevity, only the differences between brush cleaning device 100 and brush cleaning device 200 will be described in detail herein.

Brush cleaning device 200 may include an outer housing 202, an inner housing 204, a door 206, an optional display (not shown), control components 212, a sterilizing component 214, a support grill 216, at least one fan 218, and an electronic circuit 120.

The shape of the outer housing 202 may be generally rectangular. The outer housing 202 of the brush cleaning device 200 may be manufactured of a plastic or other suitable material, similar to brush cleaning device 100. Further, the outer housing 202 may include openings 202a formed along an upper surface therein and extending into the brush cleaning device 200 for receiving and securing make-up brushes "B" in the brush cleaning device 200.

The inner housing 204 may be constructed of similar materials and shape as the outer housing 202. In embodiments, the inner housing 204 may be constructed s materials similar to inner shell 104. Further, the inner housing 204 may include a comb-like retainer 204a for securing make-up brushes "B" in the brush cleaning device 200. The openings 202a of the outer housing 202 may be in registration with corresponding recesses 204b of the comb-like retainer 204a to help secure the make-up brushes "B" in the brush cleaning device 200.

Each opening 202a of outer housing 202 and each recess 204b of retainer 204a may include a polymeric or rubber-like material extending into the opening/recess and/or extending substantially orthogonally from the opening/recess. The polymeric or rubber-like material functions to increase contact or static friction with make-up brushes "B" to help secure and retain make-up brushes "B" in brush cleaning device 200. For example, each opening 202a of outer housing 202 and each recess 204b of retainer 204a may include a rubber drape 220a extending from opposite sides of the opening/recess and spanning the opening/recess to define a slit therebetween. Each opening 202a of outer housing 202 and each recess 204b of retainer 204a may further include a rubber stem 220b projecting orthogonally from the opening/recess, wherein each rubber stem 220b has a c-shaped transverse, cross-sectional profile that defines a slit that is in registration with the slit defined by the rubber drapes 220a.

Brush cleaning device 200 includes at least one fan 218 configured to circular air along the interior of the brush cleaning device 200.

In embodiments, the door 206 may be transparent, or may include at least one window, for visualizing the contents of brush cleaning device 200. The door 206 may be hinged or releasably attached to the outer housing 202 or other components of the brush cleaning device 200, and provide the user with selective access to a cleaning chamber defined within the outer housing 202 and/or the inner housing 204.

The sterilizing component 214 may include at least one UV light bulb, or the like, 214a, and, optionally, at least one heating element 214b. The sterilizing component 214 may be connected to an electronic circuit (not shown) for receiving control signals therefrom. The sterilizing component 214 may be disposed proximate a bottom of the inner housing 204. In an embodiment, the UV light bulb 214a may extend substantially an entire length of the cleaning chamber, and more specifically, the UV light bulb 214a may define a longitudinal axis that extends along a plane defined by the openings 202a of the outer housing 202 and by the recesses 204b of the retainer 204a. It is contemplated that at least a portion of the UV light bulb 214a is in registration with each opening 202a of the outer housing 202 and each recess 204b of the retainer 204a.

While in use, brush cleaning device 200 may be connected to a power source (A/C, D/C, battery, etc.) via a power cable "C", next, a make-up brush "B" may be inserted into opening 202a of outer housing 202 and into corresponding recess 204b of retainer 204a of inner housing 204, and lastly close door 206. The user then may turn on the cleaning device 200 using an on/off switch 212a of control component 212 for turning on/off the UV light bulb 214a, or an on/off switch 212b of control component 212 for turning on/off the heating element 214b. Optionally, the user may activate the fan 218 by pressing an on/off switch 212c of control component 212. Optionally, the user may activate a timer by pressing an on/off switch 212d of control component 212.

In alternate embodiments, the brush cleaning devices 100/200 may incorporate alternate or additional cleaning methods to UV light cleaning that include, but are not limited to, ultra-sonic cleaning, resistive heat cleaning, microwave heating, and/or gentle agitation. For example, the sterilizing component may be a light or/and a heating source adapted for applying at least one additional mode of treatment, selected from the group consisting of warming light treatment, infrared light treatment, white-light halogen treatment, laser treatment, microwave treatment and others.

In another alternate embodiment, the brush cleaning devices 100/200 may incorporate alternate or additional configurations to dry, sanitize, and/or disinfect elements like hair brushes, sponges, scissors, tweezers and other personal care elements.

It is contemplated that the brush cleaning devices 100/200 may include programmable settings such as, for example, temperature settings, time settings, duration settings, intensity settings, self-cleaning settings, etc.

It is understood that the brush cleaning devices 100/200 can be configured as a brush cleaner and sanitizer that can gently and efficiently clean multiple make-up brushes simultaneously.

It will be understood that various modifications may be made to the embodiments disclosed herein. For example, any of the specific elements of brush cleaning device 100 may be incorporated into brush cleaning device 200, and vice-versa. Therefore, the above description should not be construed as limiting, but merely as exemplifications of embodiments. Those skilled in the art will envision other modifications within the scope and spirit of the claims appended thereto.

What is claimed is:

1. A dryer, sanitizer, and disinfecting device for make-up brushes, the device comprising:
   an outer housing having an upper surface defining a plurality of openings therein, the plurality of openings being arranged in a linear array;
   an inner housing disposed within the outer housing, the inner housing including a retainer projecting from an inner surface thereof, wherein the retainer includes a plurality of recesses corresponding to the plurality of openings defined in the upper surface of the outer housing, wherein the plurality of recesses and the plurality of openings are in registration with one another;
   a door secured to at least one of the outer housing or the inner housing, wherein the door is configured to selectively open the device to provide access to a cleaning chamber defined by at least one of the outer housing or the inner housing, wherein the door is at least partially transparent;
   a sterilizing component supported within at least one of the outer housing or the inner housing, wherein the sterilizing component effects the cleaning chamber, wherein the sterilizing component includes a UV light bulb; and
   an electronic circuit connected to the sterilizing component for selective activation of the sterilizing component.

2. The device according to claim 1, wherein the UV light bulb extends across substantially an entire length of the cleaning chamber.

3. The device according to claim 2, wherein the UV light bulb extends along a bottom of the cleaning chamber.

4. The device according to claim 3, wherein the UV light bulb defines a longitudinal axis that extends along a plane defined by the openings of the outer housing and by the recesses of the retainer.

5. The device according to claim 4, wherein at least a portion of the UV light bulb is in registration with each opening of the outer housing and each recess of the retainer.

6. The device according to claim 5, wherein the sterilizing component includes a heating element.

7. The device according to claim 5, wherein the sterilizing component includes at least one of a heating element or a fan.

8. The device according to claim 7, further comprising control components connected to the electronic circuit and each of the UV light bulb, the heating element and the fan, wherein the control components control activation of each of the UV light bulb, the heating element and the fan.

9. The device according to claim 8, wherein the control component includes a timer.

10. The device according to claim 1, wherein each opening of the outer housing includes a rubber-like retainer extending into the opening and extending substantially orthogonally from the opening, for increasing friction with a make-up brush loaded into the device.

11. The device according to claim 10, wherein the rubber-like retainer includes a drape extending from opposite sides of the opening of the outer housing and spanning the opening to define a slit therebetween.

12. The device according to claim 11, wherein the rubber-like retainer includes a stem projecting orthogonally from the opening of the outer housing, wherein the stem has a c-shaped transverse, cross-sectional profile that defines a slit that is in registration with the slit defined by the rubber drape of the opening of the outer housing.

13. The device according to claim 10, wherein each recess of the inner housing includes a rubber-like retainer extending into the opening and extending substantially orthogonally from the opening, for increasing friction with a make-up brush loaded into the device.

14. The device according to claim 13, wherein the rubber-like retainer includes a drape extending from opposite sides of the recess of the inner housing and spanning the recess to define a slit therebetween.

15. The device according to claim 14, wherein the rubber-like retainer includes a stem projecting orthogonally from the recess of the inner housing, wherein the stem has a c-shaped transverse, cross-sectional profile that defines a slit that is in registration with the slit defined by the rubber drape of the recess of the inner housing.

* * * * *